US012611536B2

(12) United States Patent
Patel et al.

(10) Patent No.: US 12,611,536 B2
(45) Date of Patent: Apr. 28, 2026

(54) CATHETER FOR MEMBRANE BLOOD OXYGENATION

(71) Applicants: Vinod Patel, Brooklyn, NY (US); Iosif Gulkarov, Rego Park, NY (US)

(72) Inventors: Vinod Patel, Brooklyn, NY (US); Iosif Gulkarov, Rego Park, NY (US)

(73) Assignees: Vinod Patel, Brooklyn, NY (US); Iosif Gulkarov, Rego Park, NY (US)

( * ) Notice: Subject to any disclaimer, the term of this patent is extended or adjusted under 35 U.S.C. 154(b) by 329 days.

(21) Appl. No.: 18/216,767

(22) Filed: Jun. 30, 2023

(65) Prior Publication Data

US 2024/0001107 A1 Jan. 4, 2024

Related U.S. Application Data

(60) Provisional application No. 63/357,397, filed on Jun. 30, 2022.

(51) Int. Cl.
| | |
|---|---|
| *A61M 60/886* | (2021.01) |
| *A61M 1/32* | (2006.01) |
| *A61M 60/13* | (2021.01) |
| *A61M 60/38* | (2021.01) |

(52) U.S. Cl.
CPC ............ *A61M 60/886* (2021.01); *A61M 1/32* (2013.01); *A61M 60/13* (2021.01); *A61M 60/38* (2021.01); *A61M 2205/15* (2013.01)

(58) Field of Classification Search
CPC .... A61M 60/38; A61M 60/886; A61M 60/13; A61M 1/32; A61M 60/135; A61M 60/816; A61M 1/267; A61M 1/1678; A61M 2205/8206; A61M 2205/8218; A61M 2205/15
See application file for complete search history.

(56) References Cited

U.S. PATENT DOCUMENTS

| | | | | |
|---|---|---|---|---|
| 2004/0052681 A1* | 3/2004 | Mortensen | .......... | A61M 1/1625 604/6.14 |
| 2005/0119597 A1* | 6/2005 | O'Mahony | ......... | A61M 1/3661 604/4.01 |

* cited by examiner

*Primary Examiner* — Jacqueline F Stephens

(57) ABSTRACT

The present disclosure relates to intracorporeal gas exchange systems and methods in conditions associated with hypoxia and hypercarbia. The present disclosure envisages an intracorporeal oxygenation system comprising a blood oxygenator having a blood compartment and a gas compartment. The blood and gas compartments are separated by a gas permeable barrier so as to allow exchange of carbon dioxide in blood in the blood compartment with oxygen in the gas compartment. The system comprises a catheter device for insertion in a blood vessel of human comprising an interior portion and an exterior portion wherein the interior portion (100a) comprises an annular housing, a plurality of capillary conduit, a pumping device, an air sensing device, a blood sensor and a collar. The present disclosure also relates to a method of oxygenating a deoxygenated blood in a human and also to a method for treating a human suffering from hypoxia or hypercarbia.

8 Claims, 2 Drawing Sheets

CATHETER FOR MEMBRANE BLOOD OXYGENATION

CROSS-REFERENCE TO RELATED APPLICATION

This application claims priority to and the benefit of U.S. Provisional Patent Application No. 63/357,397, filed on Jun. 30, 2022, the contents of which are hereby incorporated by reference herein for all purposes.

TECHNICAL FIELD

The present disclosure relates to the field of healthcare, specifically critical respiratory care. More specifically, it pertains to intracorporeal gas exchange systems and methods and, particularly, to systems and methods to effect gas exchange within a patient's vascular structure in conditions associated with hypoxia and hypercarbia.

BACKGROUND

Respiratory failure is a condition associated with low oxygen levels and/or high carbon dioxide levels. In this condition, lungs malfunction leads to failure of blood oxygenation and removal of carbon dioxide. Standard treatment of respiratory failure includes use of mechanical ventilation, bronchodilators, proning and other medical maneuvers. If all measures fail, extracorporeal membrane oxygenation (ECMO) can be considered.

Conventional ECMO requires transport of blood outside of the body to the oxygenator, and then back to the heart/lungs, that is gas exchange occurs outside of the body, in an "extracorporeal" manner, hence the term "extracorporeal membrane oxygenation" ("ECMO"). An ECMO device processes patient blood by adding oxygen and removing carbon dioxide through fiber membrane technology, replicating the natural gas exchange function of the lungs.

ECMO is employed under circumstances of severe, reversible respiratory failure or to patients responding adversely to all advanced modes of mechanical ventilation. Operation of the circuit relies on a pump to draw blood from the vena cava, transport it through the membrane oxygenator, and return the blood either to the right atrium (veno-venous bypass) or aorta (venoarterial bypass). With less required work from the lungs, ECMO permits physiological complications to abate and the therapy can be applied for weeks barring complications. Limitations of ECMO primarily arise from external circuitry and artificial blood contacting surfaces. To avert thrombosis within the circuit, patient blood is continuously anti-coagulated and bleeding is a major risk whether internal (intercranial) or from cannula dislodgement. Patients are paralyzed and/or heavily sedated to minimize movement causing dislodgement, which creates a high-risk scenario. Also, the continuous exposure of the blood to artificial surfaces causes platelets to adhere and/or alter function (thrombocytopenia) requiring the patient to receive multiple platelet transfusions. In addition, the ECMO circuit must be constantly monitored for mechanical failures such as tubing degradation, oxygenator or pump failure, and presence of gaseous emboli or clot formation. Other noted complications include sepsis and renal failure. Finally, ECMO requires a multidisciplinary team to provide care. Staffing and overall cost of the procedure, as well as restriction to major medical centers are further limitations to providing this therapy.

WO1999044651A1 discloses an axial pump which may be introduced via the blood vessel system of a patient. The axial pump has a flexible, compressible tube which forms the pump housing. In the tube is a radially compressible rotor. The drive shaft of the rotor runs through a catheter. Together with the tube and the rotor, the catheter may be drawn into a cover hose. The radial compressibility of the components makes it possible to realise a small puncture diameter suitable for percutaneous implantation by the Seldinger technique. Through the unfolding in the heart vessel system, a relatively large pump diameter of 10 to 14 mm may be provided. This reduces the rotor speed and therefore the mechanical stress on the components. The rotor according to WO1999044651A1, has an elastic band for connecting a nitinol filament to a rotation axis. Because of this elastic connection, the filament is not perfectly centered. During pumping, this can lead to vibrations which make higher speeds or rates of pumping impossible.

U.S. Pat. No. 4,753,221A describes a catheter with an integrated blood pump which has folding blades. The blood pump is an axial pump provided with a balloon at its end. The balloon can be pumped up to unfold the pump jacket and to close the flow path leading past the pump, so fixing the pump in the blood vessel. In a further embodiment it is provided that a cup-shaped end of the catheter is arranged in a tubular guide catheter which is then withdrawn to unfold the cup-shaped end. The expandable catheter pumps have a propeller with several rigid pump blades. These are mounted pivotably. Since the blades are rigid, they cannot be made as wide as desired since, in the folded state, they would require a catheter which was too thick. Pump performance is therefore limited.

DE10059714C1 discloses an intravascular pump. The pump has a drive section and a pump section which are so small in diameter that they can be pushed through a blood vessel. A flexible cannula adjoins the pump section. To reduce flow resistance, the cannula may be expanded to a diameter which exceeds that of the drive section and pump section respectively. So that the pump may be introduced into the body by the Seldinger technique involving punctures in the blood vessel, the cannula is constricted, in which state it has a smaller diameter. In the blood vessel it is expanded so as to offer less flow resistance to the blood to be pumped.

Described in JP4126158 and EP0445782B1 respectively is an artificial heart for implantation in the body. The artificial heart has a pump section and a drive section for driving the pump section. The pump section is relatively small and serves to accommodate an axial flow pump in the form of a screw pump. Different types of screw pump are provided.

Described in EP0364293A2 is a catheter with integral blood pump. A flexible edge extends over a tubular section of the catheter and contacts the wall of the aorta, ensuring by this means that all the blood within the aorta flows through the pump. In addition, the flexible, expandable edge provides clearance between the pump and the aortic valve.

Despite improvements in the performance and design of conventional blood oxygenators, there remains a need for a more compact and efficient blood oxygenator catheter where blood doesn't have to travel outside of the body for gas exchange and reduces blood clotting and bleeding complications. Thus, there is a need for a compact, efficient, non-traumatic intracorporeal oxygenation system with blood pumping function which also facilitates its use in the body.

OBJECTS OF THE DISCLOSURE

Some of the objects of the present disclosure, which at least one embodiment herein satisfies, are as follows:

It is an object of the present disclosure to ameliorate one or more problems of the prior art or to at least provide a useful alternative;

An object of the present disclosure is to provide an intracorporeal oxygenation system for oxygenating blood within the vascular system of the human;

Another object of the present disclosure is to provide an intracorporeal oxygenation system for oxygenating blood by using minimally invasive techniques;

Still another object of the present disclosure is to provide a method for oxygenating a deoxygenated blood in a human; and Other objects and advantages of the present disclosure will be more apparent from the following description, which is not intended to limit the scope of the present disclosure.

SUMMARY

In one aspect, the present disclosure envisages an intracorporeal oxygenation system. The system comprises a blood oxygenator having a blood compartment and a gas compartment. The blood and gas compartments are separated by a gas permeable barrier so as to allow exchange of carbon dioxide in blood in the blood compartment with oxygen in the gas compartment. The system comprises a catheter device for insertion in a blood vessel of human comprising an interior portion and an exterior portion wherein the interior portion (100a) comprises an annular housing, a plurality of capillary conduit, a pumping device, an air sensing device, a blood sensor and a collar.

In another aspect, the present disclosure relates to a method of oxygenating a deoxygenated blood in a human. The method comprises initially delivering a distal end opening of the intracorporeal oxygenation system via percutaneous access into a blood vessel of a human followed by inserting the interior portion of the annular housing completely in the blood vessel incised opening. The pump regulates the flow rate control, oxygen flow rate, of the pumping device thereby causing a flow of oxygen through the gas compartment and causing the pumping device to alternate between causing blood to flow in the catheter lumen from the blood vessel to the oxygenator and causing blood to flow in the catheter lumen from the oxygenator to the blood vessel so as to allow exchange of carbon dioxide in blood in the blood compartment with oxygen in the gas compartment.

In yet another aspect of the present disclosure, disclosed is a method for treating a human suffering from hypoxia or hypercarbia comprising using the intracorporeal oxygenation system to effect gas exchange within the human's vascular structure.

BRIEF DESCRIPTION OF THE DRAWINGS

For a more complete understanding of the present disclosure, reference is now made to the following description taken in conjunction with the accompanying drawings.

DETAILED DESCRIPTION

The detailed description set forth below, in connection with the appended drawing, is intended as a description of various configurations and is not intended to represent the only configurations in which the concepts described herein may be practiced. The detailed description includes specific details for the purpose of providing a thorough understanding of the various concepts. It will be apparent to those skilled in the art, however, that these concepts may be practiced without these specific details. As described herein, the use of the term "and/or" is intended to represent an "inclusive OR", and the use of the term "or" is intended to represent an "exclusive OR".

The disclosure will now be described with reference to the accompanying embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Figure 1:
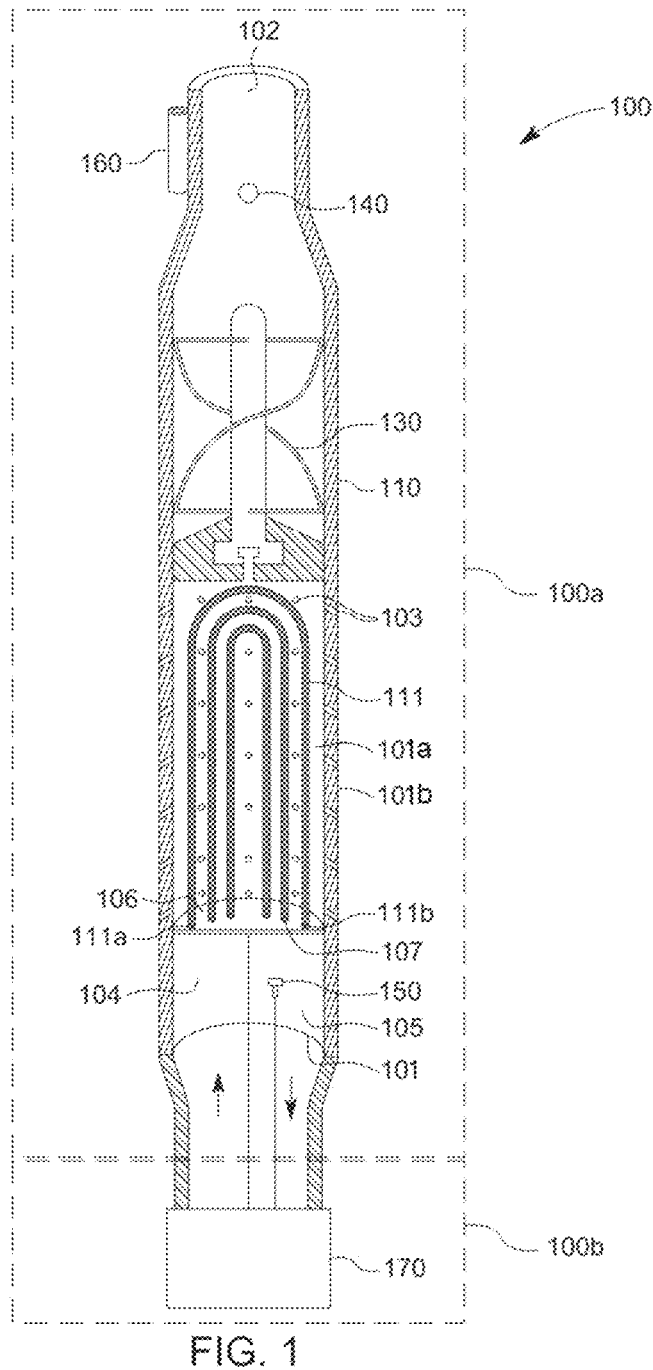
FIG. 1 illustrates the blood oxygenator inside the inferior vena cava blood vessel.
Figure 2:
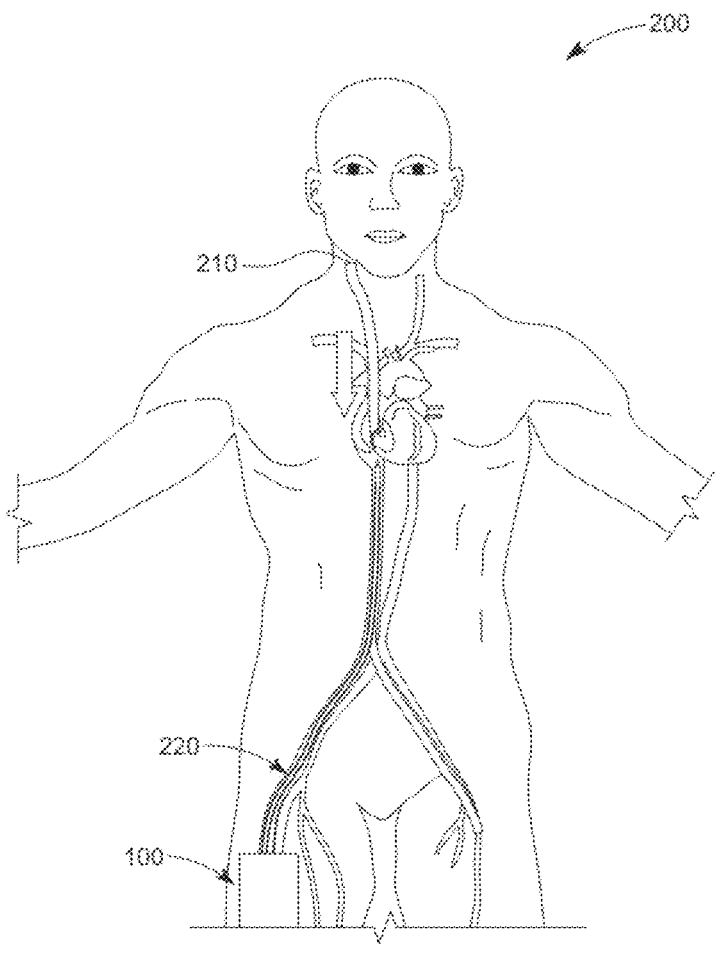
FIG. 2 illustrates the blood oxygenator insertion route in the body.

In one aspect, the present disclosure envisages an intracorporeal oxygenation system. FIG. 1 provides a general, perspective sectional view of the intracorporeal oxygenation system 100. The system comprises a blood oxygenator having a blood compartment and a gas compartment. The blood and gas compartments are separated by a gas permeable barrier so as to allow exchange of carbon dioxide in blood in the blood compartment with oxygen in the gas compartment. The system comprises a catheter device for insertion in a blood vessel of human comprising an interior portion and an exterior portion wherein the interior portion (100a) comprises an annular housing, a plurality of capillary conduit, a pumping device, an air sensing device, a blood sensor and a collar.

In an exemplary embodiment of the present disclosure, the catheter device is inserted in the inferior vena cava or the superior vena cava of human.

In an embodiment of the present disclosure, the annular housing (110) is configured to be inserted at a controlled depth into the vascular system of the patient having a proximal end opening (101), a distal end opening (102), a longitudinally extending linking portion between the proximal end opening and the distal end opening and at least two chambers inside the lumen of the annular housing, vertically extending from the proximal end opening of the annular housing towards the distal end opening of the annular housing.

In one embodiment, the oxygen rich air flows into the annular housing 110 via first proximal end 101a of the first chamber 104. The $CO_2$ rich air exits through the second proximal end 101b of second chamber 105. In an exemplary embodiment of the present disclosure, the air (circulating air) is used to rotate a pre-determined motor to fulfil the requirement of using a power source. This circulating air is used as a source of pneumatic power. Thus, the system can be powered by electricity or battery or pneumatic air source or a combination thereof.

Typically, the annular housing 110 is made from any suitable biocompatible material.

In another exemplary embodiment of the present disclosure, the longitudinally extending linking portion comprises a plurality of pores (103) for inflow of blood from the vascular system into the annular housing (110).

In yet another exemplary embodiment of the present disclosure, the at least two chambers comprise a first chamber (104) and a second chamber (105) separated by a vertically planar surface along the central axis of the annular housing. Typically, the distal ends of the first chamber (104) and the second chamber (105) are sealed with at least one radially non-collapsing disc (106) comprising a plurality of apertures (107) arranged along radii of the disc.

In another embodiment of the present disclosure, the plurality of capillary conduit (111) is configured to be positioned in the lumen of the annular housing between distal end of the chambers and distal end of the annular housing. Typically, the capillary conduit comprises a first end portion (111a) and a second end portion (111b) and a longitudinally extending linking portion between the first end portion and the second end portion.

The plurality of capillary conduit is a semi-permeable membrane in contact with the blood present in the lumen of the annular housing wherein the oxygen flowing in the plurality of capillary conduit is diffused into the deoxygenated blood and carbon dioxide is diffused in the capillary conduit.

In still another exemplary embodiment of the present disclosure, the first end portion (111a) and the second end portion (111b) are configured to mate with at least a portion of the plurality of apertures (107) on the radially non-collapsing disc (106) located on the distal end of at least one chamber.

In an exemplary embodiment, the capillary conduit 111 is made from semi-permeable membrane which is configured to be in contact with the deoxygenated blood present in the lumen of the annular housing 110, wherein the oxygen flowing in the plurality of capillary conduit is diffused into the deoxygenated blood and carbon dioxide is diffused in the capillary conduit 111. In one embodiment the flow of $O_2$ rich gases is unidirectional, wherein the $O_2$ rich air flows through the capillary conduit from first end portion and exits from second end portion of the capillary conduit 111 after exchanges of gases. The capillary conduit 111 is a semiper-meable membrane that allows diffusion of $O_2$ into the deoxygenated blood; simultaneously it facilitates the diffusion of $CO_2$ from deoxygenated blood into the capillary conduit 111. In an alternative embodiment, the plurality of capillaries conduit 111 comprises a membrane oxygenation core through which oxygen flows.

In one embodiment, the semipermeable membrane material of capillaries conduit 111 is selected from a group consisting of polymer, silicone and other suitable material used for gas exchange. Further, the capillary conduit 111 diameter is suitably selected to enhance the effective diffusion of oxygen into the blood. This ensures a higher surface area for oxygen-blood interaction and maximum diffusion of oxygen into the blood. In one embodiment, the flow rate of oxygen rich gas in first chamber is suitably selected to achieve maximum gas exchange at the blood-membrane interface.

In yet another embodiment of the present disclosure, the pumping device (130) is configured to be positioned within the lumen and distal end of the annular housing such that the pumping device draws blood from a blood vessel into the annular housing for oxygenation and pumps out oxygenated blood.

In an exemplary embodiment of the present disclosure, the pumping device (130) is bidirectionally operable.

The pumping device 130 is positioned in the lumen of annular housing in such a manner that oxygenated blood flows through head of the pumping device only. In an exemplary embodiment, the pumping device is irremovably fixed at distal end of the annular housing. In an exemplary embodiment, the blood drawn into the lumen of the annular housing 110 which is driven by negative pressure created by an axial motor 130 located distally to the plurality of pores 103.

In one embodiment, the oxygenated blood in the lumen of the annular housing 110 drains through the distal end opening 102 of the annular housing 110, back into the vascular system via pumping device 130. In some embodiment, the oxygenated blood is drained into inferior vena cava or right atrium. This ensures that oxygenated blood in the annular housing 110 is well drained by pumping device 130, thus maintaining optimal flow to achieve efficient gases exchange.

In some embodiment, the motor pump 130 is connected to an external device positioned in the exterior region 300 of the catheter system 100 via wired source or wireless source and microprocessor controller. In some embodiment, the motor pump 130 flow rate is proportional to the oxygen flow rate inside the plurality of capillary conduit 111.

In still another embodiment of the present disclosure, the air sensing device (140) is configured to be positioned within the proximity of the motor pump.

In an exemplary embodiment of the present disclosure, the sensing device comprises an air sensor to detect gas leakage within the distal end of the pumping device. In one embodiment, an air sensor 140 is placed within proximity of pumping device 130 to detect leakage of air from the plurality of capillary conduit 111. The air sensor 140 upon detection of gas bubbles leads to shutdown of the device and/or halting the flow of oxygen in first chamber 104.

In yet another embodiment of the present disclosure, the blood sensor (150) is positioned within the second chamber of the annular housing configured to detect any blood leakage within the second chamber.

In one of the exemplary embodiments, a blood sensor 150 is configured to be positioned in second chamber of the annular housing 110. In one embodiment, the blood sensor 150 detects presence of blood in the second chamber 105 of the annular housing 110 if any blood from lumen of annular housing enters into plurality of capillary conduit 111 or plurality of apertures 107 arranged along area of the disc 106 located on top of the second chamber 105. The blood sensor 150 upon detection of blood would lead to shutdown of the device.

In still another embodiment of the present disclosure, the collar (160) is positioned on the distal end of the annular housing extending distally along the axis parallel to the central axis of the annular housing. The external surface of the collar is irremovably attached to external surface of the annular housing at the distal end.

In yet another exemplary embodiment of the present disclosure, the collar 160 is configured to be positioned along the outer circumferential surface, at the distal end of the annular housing 110, wherein the collar extends longitudinally along the axis parallel to the central axis of the annular housing 110. In one embodiment, the collar 160 is hollow cylindrical segment, wherein a guidewire can be removably drawn in the collar 160. The guidewire when drawn within the central axis in collar in to the vascular system, the inner portion 100a of the catheter system 100 can be placed into an area of interest with the help of guidewire removably attached to the collar 160. In one embodiment, the collar 160 of the catheter system 100 incorporates an opening for guidewire, to allow insertion of the catheter system 100 over a guidewire.

In one embodiment, the exterior portion of catheter 100 is connected to the console box 170. The console box 170 is configured to control the gas flow, gas tubing, opening for gas egress, tubing for infusion of an anticoagulant solution, motor speed control.

In still another exemplary embodiment of the present disclosure, system can be placed in the arterial system (aorta) in conditions like aortic coarctation.

In another aspect, the present disclosure relates to a method of oxygenating a deoxygenated blood in a human. The method comprises initially delivering a distal end opening of the intracorporeal oxygenation system via percutaneous access into a blood vessel of a human followed by inserting the interior portion of the annular housing completely in the blood vessel incised opening. The catheter device is inserted percutaneously over a wire with image guidance. The catheter device is inserted through the incised opening of the blood vessel.

The pump regulates the flow rate control, oxygen flow rate, of the pumping device thereby causing a flow of oxygen through the gas compartment and causing the pumping device to alternate between causing blood to flow in the catheter lumen from the blood vessel to the oxygenator and causing blood to flow in the catheter lumen from the oxygenator to the blood vessel so as to allow exchange of carbon dioxide in blood in the blood compartment with oxygen in the gas compartment. The pump regulates the external oxygen flow rate, partial oxygen pressure and $CO_2$ pressure in synchronization with the blood flow rate of the pumping device such that oxygenation of deoxygenated blood is achieved efficiently.

In an alternative embodiment, the system is inserted through the opening of the blood vessel. In still another exemplary embodiment of the present disclosure, the annular housing is completely inserted in the blood vessel via incised opening followed by adjusting the flowrate of the pumping device and external oxygen supply. In another embodiment of the present disclosure, the external oxygen flow rate is adjusted in synchronization with flowrate of the pumping device such that oxygenation of deoxygenated blood is achieved efficiently.

In yet another aspect of the present disclosure, disclosed is a method for treating a human suffering from hypoxia or hypercarbia comprising using the intracorporeal oxygenation system to effect gas exchange within the human's vascular structure.

EXPERIMENTAL SECTION

Pilot Studies

A total of 5 pilot experiments were conducted to determine stability of the present system. All animals demonstrated remarkable hemodynamic stability during support on the system, with no evidence of acidosis or increasing lactate, decreasing circuit flows, or circulatory failure. Unexpectedly, two animals displayed bradycardia immediately upon initial opening of circulation, requiring the administration of epinephrine and atropine to restore normal cardiac function. Following this initial event, no animals required vasopressor support at any time in the run.

Tortuous Loop Component Tests.

The following provides a brief discussion of tests and results of component function in a tortuous environment. The tests were also beneficial for determining the system suitable to retain flexibility. The system was tested in the tortuous loop setup to evaluate torque requirements, fatigue, and impeller length.

The testing device was placed in a loop and water was circulated to provide a fluid environment. Torque was calculated by measuring the current into the drive system and converting by means of the motor torque constant.

The results of all testing indicated that, the system could withstand rotation at 20,000 rpm in the tortuous loop and provided the largest inner diameter to reduce resistance against sweep gas flow.

Effect of Fluid Viscosity on Torque.

Testing was performed in a straight test section to evaluate whether fluid viscosity would have a noticeable effect on torque transmission. This was done to ensure that testing in water was suitable and that an increase in viscosity to that of blood would not add excessive torque to the motor or tubing that should be considered. The test was performed using tubing sample A in both water and air. The results depict that fluid viscosity had a negligible effect on the system of the present disclosure.

TECHNICAL ADVANCES AND ECONOMICAL SIGNIFICANCE

The intracorporeal oxygenation system of the present disclosure described herein above has several technical advantages including but not limited to the realization of:

a system having a relatively small size which is beneficial for intracorporeal/intravascular respiratory assist devices and insertion;

a system with reduced insertion size which is desirable to prevent tissue damage and facilitate placement; and a system with an increase in gas exchange efficiency and is limited by potential damage to surrounding tissue and to the blood.

While the disclosure has been particularly shown and described with reference to specific embodiments, it should be understood by those skilled in the art that various changes in form and detail may be made therein without departing from the spirit and scope of the disclosure as defined by the appended claims. For example, membrane shapes other than housing that also exhibit high gas exchange may be used. Further, the oxygenator catheter may be integrated into a device that also encompasses other functions, such as blood filtration to augment renal and other organ functions. For example, relational terms, such as "above" and "below' are used with respect to a view of the device as shown in the present disclosure. Of course, if the device is inverted, above becomes below, and vice versa. Additionally, if oriented sideways, above and below may refer to sides of a device. Moreover, the scope of the present application is not intended to be limited to the particular configurations of the process, machine, manufacture, and composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding configurations described herein may be utilized according to the present disclosure. The scope of the disclosure is indicated by the appended embodiments, and all changes which come within the meaning and range of equivalency of the embodiments are intended to be embraced.

The description of the disclosure is provided to enable any person skilled in the art to make or use the disclosure. Various modifications to the disclosure will be readily apparent to those skilled in the art, and the generic principles defined herein may be applied to other variations without departing from the spirit or scope of the disclosure. Thus, the disclosure is not intended to be limited to the examples and designs described herein but are to be accorded the widest scope consistent with the principles and novel features disclosed herein.

This has outlined, rather broadly, the features and technical advantages of the present disclosure in order that the detailed description that follows may be better understood. Additional features and advantages of the disclosure will be described below. It should be appreciated by those skilled in the art that this disclosure may be readily utilized as a basis for modifying or designing other structures for carrying out the same purposes of the present disclosure. It should also be realized by those skilled in the art that such equivalent constructions do not depart from the teachings of the disclosure as set forth in the appended claims. The novel features, which are believed to be characteristic of the disclosure, both as to its organization and method of operation, together with further purposes and advantages, will be better understood from the following description when considered in connection with the accompanying figures. It is to be expressly understood, however, that each of the figures is provided for the purposes of illustration and description only and is not intended as a definition of the limits of the present disclosure.

Although several embodiments have been described in detail for purposes of illustration, various modifications may be made without departing from the scope and spirit of the present disclosure. Accordingly, the disclosure is not to be limited by the examples presented herein, but is envisioned as encompassing the scope described in the appended claims and the full range of equivalents of the appended claims.

The invention claimed is:

1. An intracorporeal oxygenation system (100) said system comprising a blood oxygenator having a blood compartment and a gas compartment, said blood and gas compartments being separated by a gas permeable barrier so as to allow exchange of carbon dioxide in blood in said blood compartment with oxygen in said gas compartment characterized in that said system (100) comprises a catheter device for insertion in a blood vessel of human comprising an interior portion (100*a*) and an exterior portion (100*b*); wherein said interior portion (100*a*) comprises:

an annular housing (110) configured to be inserted at a controlled depth into the vascular system of the patient having a proximal end opening (101), a distal end opening (102), a longitudinally extending linking portion between said proximal end opening and said distal end opening and at least two chambers inside the lumen of said annular housing, vertically extending from said proximal end opening of the annular housing towards said distal end opening of said annular housing;

a plurality of capillary conduit (111) configured to be positioned in said lumen of said annular housing between distal end of said chambers and distal end of said annular housing wherein said capillary conduit comprises a first end portion (111*a*) and a second end portion (111*b*) and a longitudinally extending linking portion between said first end portion and said second end portion;

a pumping device (130) configured to be positioned within the lumen and distal end of the annular housing such that said pumping device draws blood from a blood vessel into said annular housing for oxygenation and pumps out oxygenated blood;

an air sensing device (140) configured to be positioned within the proximity of a motor pump comprising an air sensor to detect gas leakage within the distal end of said pumping device;

a blood sensor (150) configured to be positioned within said second chamber of said annular housing which detects any blood leakage within said second chamber;

a collar (160) configured to be positioned on said distal end of said annular housing extending distally along the axis parallel to the central axis of said annular housing;

wherein said at least two chambers comprise a first chamber (104) and a second chamber (105) separated by a vertically planar surface along the central axis of the annular housing;

wherein said distal ends of said first chamber (104) and said second chamber (105) are sealed with at least one radially noncollapsing disc (106) comprising a plurality of apertures (107) arranged along radii of the disc; and wherein said first end portion (111*a*) and said second end portion (111*b*) are configured to mate with at least a portion of said plurality of apertures (107) on said radially non-collapsing disc (106) located on said distal end of at least one chamber.

2. The system as claimed in claim 1, wherein said catheter device is inserted in the inferior vena cava or the superior vena cava of human.

3. The system as claimed in claim 1, wherein said annular housing (110) is made from any suitable biocompatible material.

4. The system as claimed in claim 1 wherein said longitudinally extending linking portion comprises a plurality of pores (103) for inflow of blood from said vascular system into said annular housing (110).

5. The system as claimed in claim 1, wherein said plurality of capillary conduit is a semipermeable membrane in contact with the blood present in said lumen of said annular housing wherein said oxygen flowing in said plurality of capillary conduit is diffused into said deoxygenated blood and carbon dioxide is diffused in said capillary conduit.

6. The system as claimed in claim 1 wherein said external surface of said collar is irremovably attached to external surface of said annular housing at the distal end.

7. The system as claimed in claim 1 wherein said pumping device (130) is bidirectionally operable.

8. The system as claimed in claim 1, wherein said system is powered by at least one selected from electricity, battery, pneumatic air source or a combination thereof.

\* \* \* \* \*